United States Patent
Erbel et al.

(12)

(10) Patent No.: US 6,792,074 B2
(45) Date of Patent: Sep. 14, 2004

(54) METHOD FOR PRODUCING OR UPDATING RADIOTHERAPY PLAN

(75) Inventors: Stephan Erbel, München (DE); Stephan Fröhlich, Aschheim (DE)

(73) Assignee: BrainLAB AG, Kirchheim/Heimstetten (DE)

( * ) Notice: Subject to any disclaimer, the term of this patent is extended or adjusted under 35 U.S.C. 154(b) by 0 days.

(21) Appl. No.: 09/898,910

(22) Filed: Jul. 3, 2001

(65) Prior Publication Data

US 2002/0122530 A1 Sep. 5, 2002

(30) Foreign Application Priority Data

Mar. 5, 2001 (EP) .......................... 01 104 553
May 25, 2001 (EP) .......................... 01 112 059

(51) Int. Cl.[7] .............................. A61N 5/10
(52) U.S. Cl. ....................................... 378/65
(58) Field of Search .......................... 378/65

(56) References Cited

U.S. PATENT DOCUMENTS 5,373,844 A    12/1994  Smith et al.
5,661,773 A  *  8/1997  Swerdloff et al. ............. 378/65

FOREIGN PATENT DOCUMENTS

DE    199 12 708 A    9/2000

OTHER PUBLICATIONS

Wells et al: "a medical expert system approach using artificial neural networks for standardized treatment planning" *International Journal of Radiation Oncology Biology Physics*, Bd. 41, Nr. 1, pp. 173–182, Apr. 1998.

Löf et al.: "An adaptive control algorithm for optimization of intensity modulated radiotherapy considering uncertainties in beam profiles, patient set–up and internal organ motion", *Physics in Medicine and Biology*, Bd. 43, pp. 1605–1628 Jun. 1998.

Yan, Di. "On–line Strategy of Daily Dose Prescription in Adaptive Radiotherapy," $22^{nd}$ *Annual EMBS Conference*. (2000): 2145–2148.

\* cited by examiner

*Primary Examiner*—Craig E. Church
(74) *Attorney, Agent, or Firm*—Renner, Otto, Boisselle & Sklar, LLP

(57) ABSTRACT

The invention relates to a method for producing or updating a radiotherapy plan within the framework of inversely planned radiotherapy, wherein an up-to-date radiotherapy plan is calculated at least partly on the basis of the results of an already existing, approved, older plan.

16 Claims, 5 Drawing Sheets

METHOD FOR PRODUCING OR UPDATING RADIOTHERAPY PLAN

The present invention relates to the field of radiotherapy, in particular radiation therapy or radio-surgery. In particular, it concerns producing or updating radiotherapy plans, and here also specifically with radiotherapy plans within the framework of inverse radiotherapy planning.

Work in radiotherapy using inverse planning is computer-assisted, pre-set data being entered into a computer system with respect to the desired dosage distribution in the target area and with respect to the organs to be protected. On this basis, the system is supposed to generate a dosage plan which ensures the best possible treatment. Since for medical reasons, the patient's therapy in the extra-cranial area is usually fractionated, i.e. radiation exposure is carried out in a number of sessions spaced out in time, it is not guaranteed that the position of the internal organs and of the target area inside the patient correspond to the positions determined in a previous examination of the patient. For this reason, a dosage distribution found to be correct for an earlier session does not for the most part correspond to a correct dosage distribution for a subsequent session.

The correspondence between the positions in the plan and the positions during radiotherapy, however, is relatively good if the patient is not relocated between the point in time at which he is subjected to an imaging procedure and the point in time of radiation exposure. If the patient is scanned again before each radiation exposure, however, new positions for the organs and the target volume result, so that an earlier treatment plan cannot in theory be adopted.

If, however, a new treatment plan is produced for each radiotherapy session, as has been usual to date, the expenditure involved in this is problematic for clinical use. This is because a high expenditure of labour is involved in producing an inverse radiotherapy plan.

A radiotherapy plan should as far as possible have the result that the target volume is completely radiated with the desired dosage; the dosage to the organs to be protected, however, remaining low. Above all in target areas which are relatively close to critical organs, the calculated plan is therefore always a compromise between the dosage distribution of the target volume and of endangered organs. The result of calculating an inverse dosage plan is assessed by way of the dosage-volume histograms. These histograms show what percentage proportion of the volume of a target area or organ absorbs what dosage. How good the resulting compromise can be depends essentially on the position of the target volume relative to the organs to be protected. Whether the calculated inverse plan more protects the critical organs or irradiates the target volume with an almost optimal dosage depends essentially on the pre-set data entered into the planning program.

FIG. 1 shows an embodiment variant for restricting the range in the dosage-volume histograms for the left and right optic nerve. The curve of the finished plan must run below the inserted squares on the left, in order to fulfil the restriction.

FIG. 2 shows an embodiment variant for restricting the range in the dosage-volume histograms for the target volume. The curve of the finished plan must run above the inserted square on the right, in order to fulfil the restriction.

FIG. 3 shows dosage-volume histograms of a calculated inverse plan. Both for the target volume (left) and for the brain stem (right), the course of the curve fulfils the pre-set data (squares).

The pre-set data, which are preferably realised as restrictions of the range for the dosage-volume histograms, are essential to the quality of the resulting plan and heavily dependent on the relative position and size of target volumes and organs to be protected. Accordingly, the high expenditure of labour already mentioned is necessary for producing these pre-set data.

In addition, it is in no way certain that all the pre-set data can actually be kept to by the planning software. Typically, some sort of compromise is proposed in this case. It is therefore not unusual for the pre-set data to have to be iteratively adapted to the result of the plan, and then a new plan has to be calculated. The next, equally work-intensive step is the acceptance (approval) of the plan, preferably by a physician. A plan is only approved when the physician is of the opinion that the compromise found is expedient and could result in as optimal a treatment for the patient as possible. To this end, the physician will preferably consider the dosage-volume histograms, since these provide the best overview of the compromise found.

A further point is that, if a "fresher" data set of the patient is recorded before the treatment, the respective target volume and the endangered organs must also be drawn in again for calculating a new plan, since the interior of the patient can shift between the different treatment appointments. This approach, however, causes problems because the expenditure of time and money for recording a data set is relatively high. Not only must the actual target volume be detected but also an adjacent volume, because the knowledge of its radioparency is necessary for dosage planning. It is also necessary to detect a larger volume partly in order to know the position of the markings which are later used for positioning the patient. Furthermore, it is often very unpleasant for an immobilised patient to have to spend a long time between producing a new image data set and radiation exposure, if the new planning takes a long time.

If, a computer tomograph or another X-ray based method is used for recording the new data set, then the patient is exposed to a radiation load roughly proportionally to the detected volume.

It is the object of the present invention to provide a method for producing or updating a radiotherapy plan, which overcomes the above disadvantages. In particular, the expenditure for producing the plan is to be reduced. A further aim of the invention is to enable a new data set to be produced for example every day, within a period of time which is short enough that the patient can remain fixed and immobilised on a treatment bed during this time.

This object is solved in accordance with the invention by a method for producing or updating a radiotherapy plan within the framework of inverse planned radiotherapy, whereby an up-to-date radiotherapy plan is calculated at least partly on the basis of the results of an already existing, approved, older plan. In other words, the information from the older radiotherapy plan which is suitable for "re-utilisation", i.e. which can simplify producing the new radiotherapy plan, is also used for calculating the new radiotherapy plan, in particular inverse calculating with computer-assistance. This deviates from previous practice which discarded the older radiotherapy plan, and in particular through this an inverse plan can be re-calculated with little expenditure of time and labour. In an advantageous embodiment, the dosage distribution of an older, conventionally or inversely produced radiotherapy plan which was found to be "OK" is used as a pre-set value for the re-calculation. On the one hand, this means that, the inverse plan can actually with very great probability also be calculated by keeping to all the pre-set values, and on the other hand the dosage distribution considered to be medically appropriate and released by the physician or physicist is (almost) capable of being reproduced.

The pre-set values for calculating the radiotherapy plan can be determined from the results of a previously calculated plan.

In addition, the method invented provides the possibility of possibly also using the knowledge of the approximate form of the target volume and of the organs, in order to reduce the expenditure of time which arises by drawing in the contours.

The third advantage of the method represented here is the reduction in the expenditure of time and money associated with recording a new data record and of the radiation load upon the patient.

Preferred and advantageous embodiments of the method in accordance with the invention are defined by the sub-claims.

Figure 1:
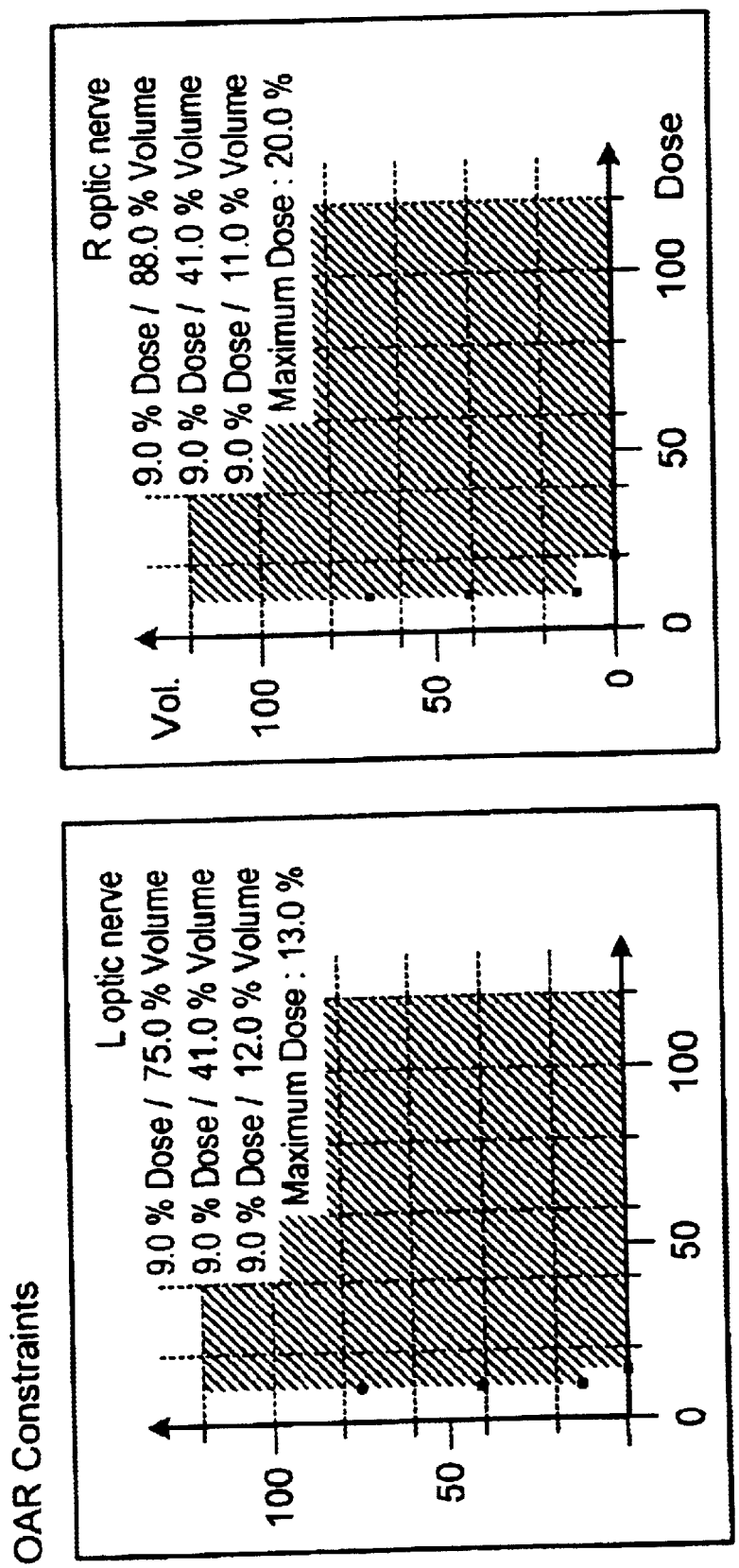
FIG. 1 illustrates a pair of exemplary dosage-volume histograms for left and right optic nerves to be used in accordance with the present invention.
Figure 2:
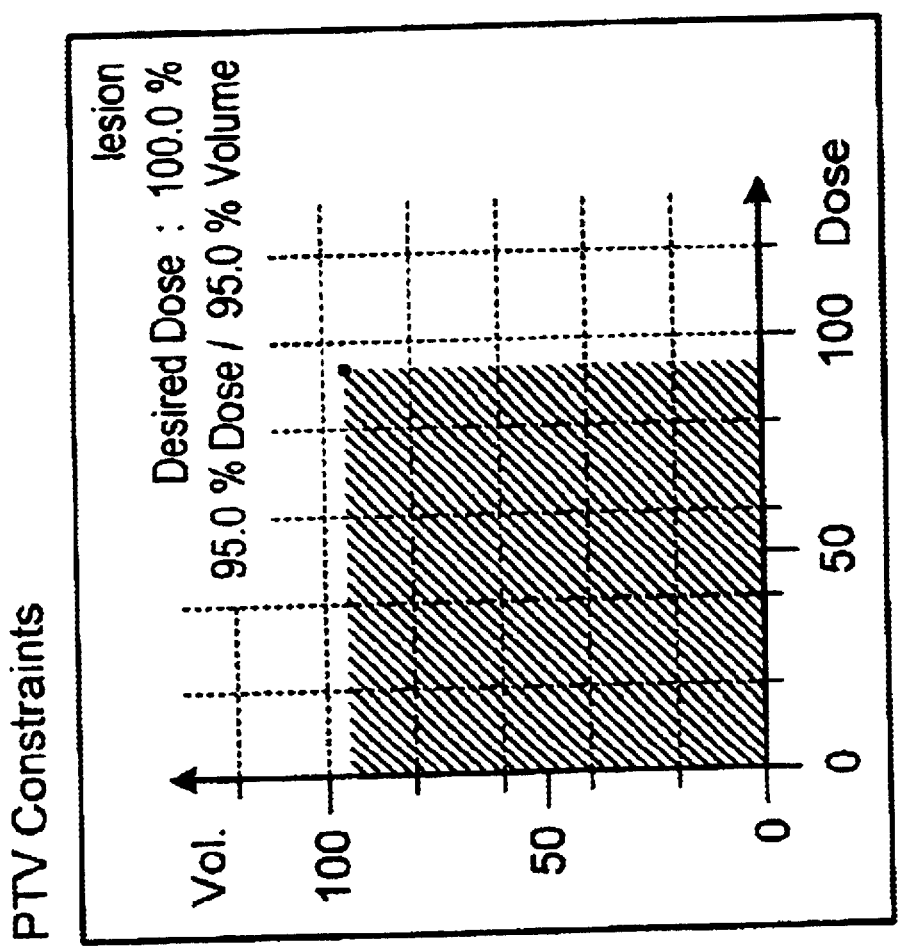
FIG. 2 illustrates an exemplary dosage-volume histogram for a target volume to be used in accordance with the present invention.
Figure 3:
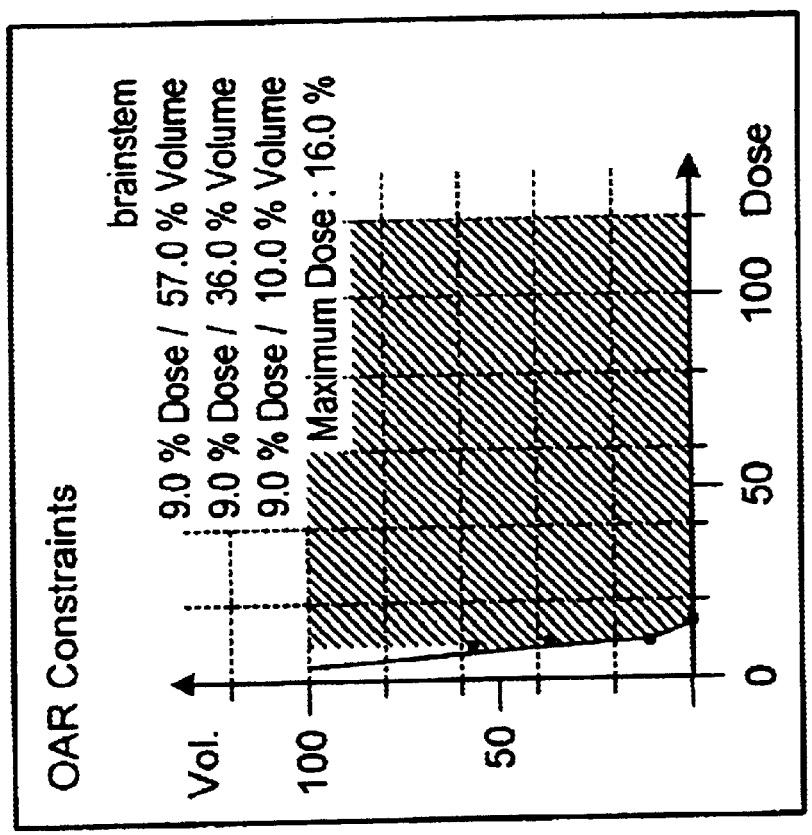
FIG. 3 illustrates a pair of exemplary dosage-volume histograms for the target volume (left) and the brain stem (right) corresponding to a calculated inverse plan to be used in accordance with one embodiment of the present invention.
Figure 3:
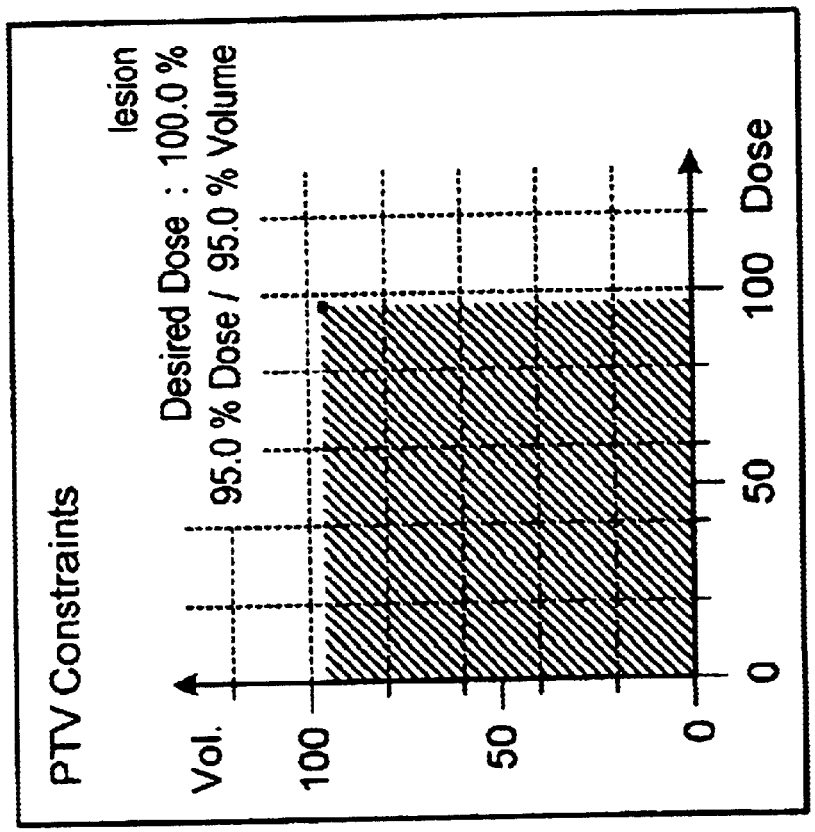

Details of the embodiments of the method in accordance with the invention are described in the following:

The inverse plan is recalculated such that, instead of a physician or physicist having new parameters for the volume-dosage histograms produced as described above, which possibly cannot be fulfilled or may not lead to satisfactory results, the parameters of the last satisfactory plan are adopted, possibly with a certain relief of the pre-set data such that the success of producing the inverse plan is almost guaranteed.

Once the new plan has been calculated, it can be determined on the basis of the volume-dosage histograms how greatly the new plan differs from the old plan. If the deviations between the new plan and the already approved plan are within a previously defined tolerance range, then a re-evaluation and approval of the plan by a physician or physicist may be omitted. This correspondingly leads to a significant reduction in the expenditure of labour required.

Thus, through the method in accordance with the invention, the time required, within which in particular the necessary working time of highly qualified persons which is required for producing a new dosage plan, can be substantially reduced, such that this approach is better suitable for clinical use.

The form and position of target volumes and of organs are transferred from an older data set into a newer data set by overlaying the data of the fresh data set onto the data of the original data set used to produce the first plan, for example graphically using image fusion. This can be realised by a number of commercially available therapy planning programs (for example BrainSCAN™ of the firm BrainLAB AG, Heimstetten). In both data sets, the visible bone structure respectively serves as the reference. Once this is completed, the contours of the target volume and of the organs can then be adopted into the new plan. Possible shifts of the objects visible in the new data set can be transferred manually or automatically onto the corresponding objects. Since the shifts relative to the bone reference are for the most part small, this repositioning of the objects is preferably an automatic, three-dimensional fusion of the drawn in objects onto the gradients of the new data.

This fusion is preferably based on elastically re-forming (morphing) the objects of the new data set. A considerable advantage of such a fusion, compared to a fusion of the raw data, is that the contours drawn in by a physician are partly based on anatomical knowledge and therefore contain more information than the recorded data itself.

If this method fails in some cases, the objects may be manually shifted. An advantage of this manual or (semi-) automatic fusion is that the arrangement between the range restrictions of the various dosage-volume histograms and the relevant organs or target volumes remains unchanged. This saves time and also reduces the risk of an incorrect arrangement due to human error.

In accordance with the invention, the recording of fresh planning data of the patient can be optimised by accessing already existing data from previous treatments and recordings by imaging devices.

In order to minimise the time, costs and the radiation load to the patient, preferably only the area of the patient in which the tumour and the endangered organs are situated is detected in accordance with the invention. This can be realised by purposefully positioning the patient relative to the imaging device, and the recorded layers or volume section are exactly coordinated. For example, even just a few new CT layer images are sufficient to "freshen up" the plan and/or data set, if one proceeds as follows: an image detection plane of an imaging device, with the aid of which the planning data set is to be updated, is determined by introducing a calibration phantom into the image recording range (which comprises markings which can be detected both by image recording and also by an external tracking system), and for the detected images a spatial relationship with the patient markings which are not detected in image recording is produced. The missing information for calculating the dosage plan, concerning the radiation absorption coefficients (Houndsfield values) of the surrounding body area, is then supplemented by a new data set by a preferably automatic fusion of the data from a previous planning data set.

In order to be able to position the patient correctly for radiation exposure, without therefore having to detect a large volume in the data set, the imaging system is—as already indicated above—preferably combined with a system which can detect external markings on the patient (for example, ExacTrac™ of the firm BrainLAB AG, Heimstetten). The external markings can then also be detected outside the recording range of the imaging system. It is then necessary for the system which detects the external markers to be calibrated relative to the imaging system, such that the position of the markers can be referenced relative to the recorded layers or to the recorded volume. Because the distance between the markings can be substantially greater (lever effect) than the distance between markings within the reduced recording range of the imaging system, the patient can then be positioned with great precision by means of a similar type of system, in order to detect the external markings on the treatment system.

Figure 4:
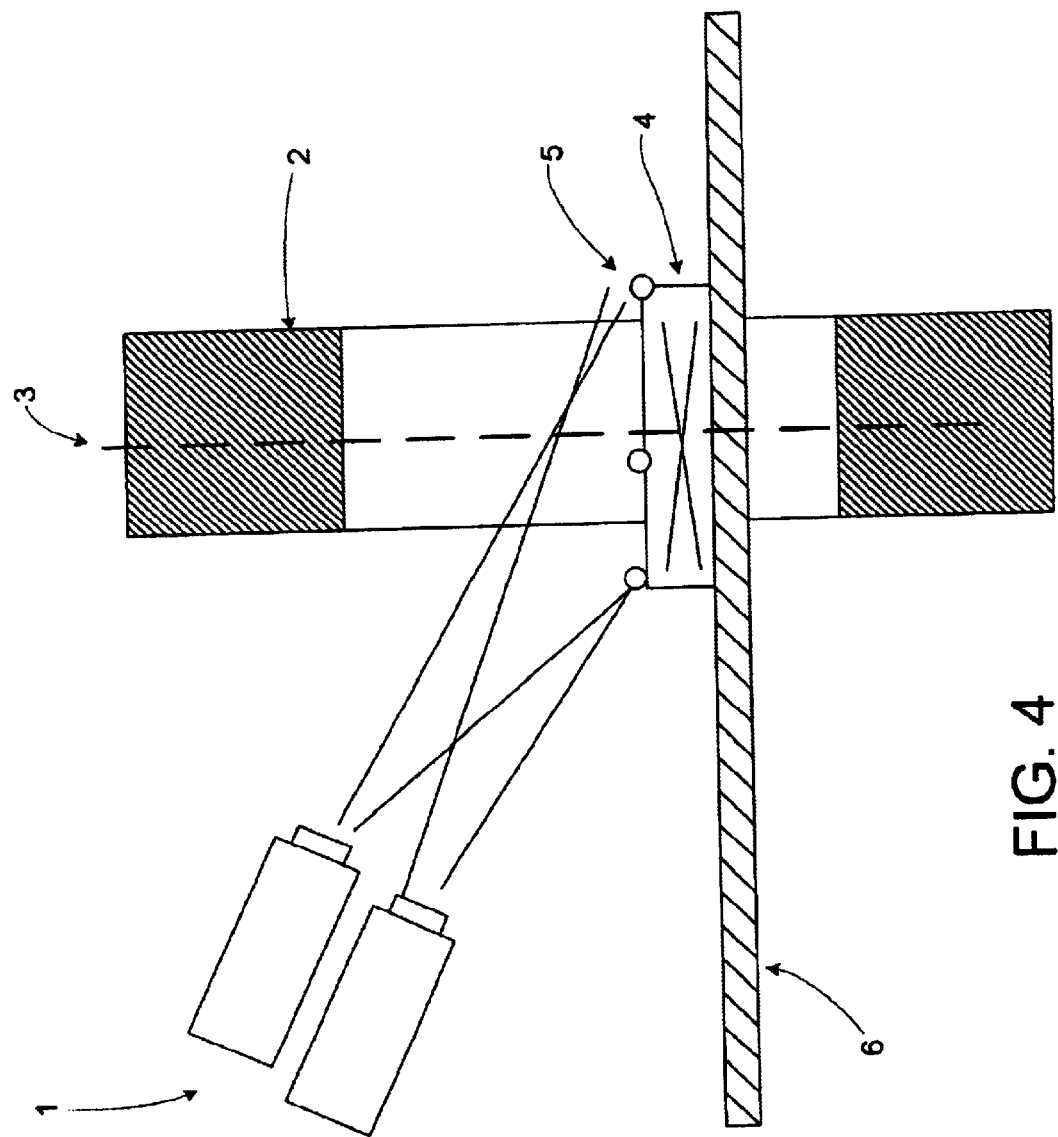
FIG. 4 is a diagrammatic illustration of a computer tomograph system including a calibration phantom for use in conjunction with the present invention.
Figure 5:
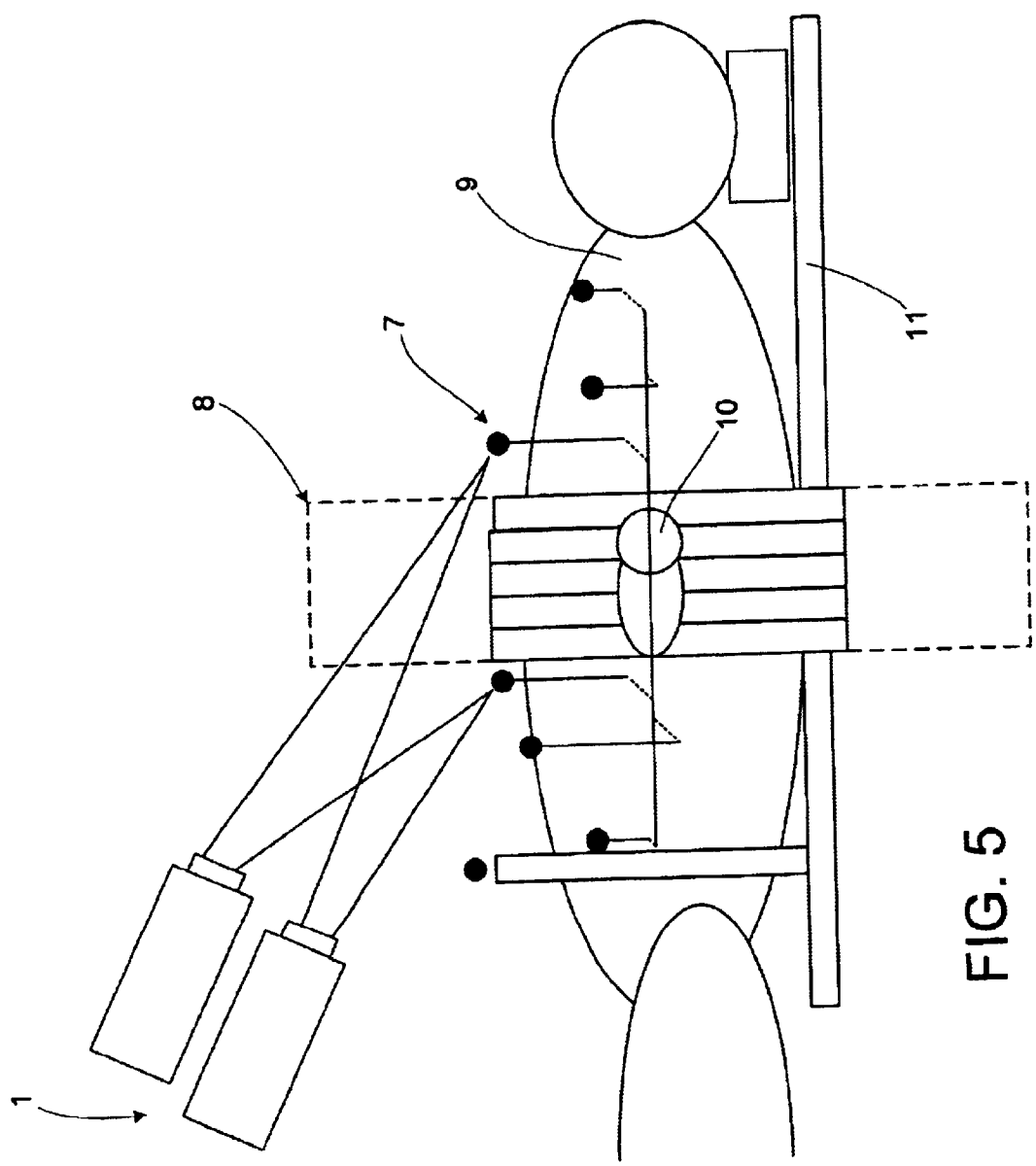
FIG. 5 is a diagrammatic illustration of a computer tomograph system used to detect the position of a patient for use in conjunction with the present invention.

Calibrating and determining the position of the patient will now be explained in more detail by way of the enclosed FIGS. 4 and 5, which show:

FIG. 4 an illustration of determining the image recording plane of a computer tomograph by means of a calibration phantom; and FIG. 5 an illustration to explain detecting the position of the patient.

FIG. 4 shows a computer tomograph having the reference numeral 2, whose image recording plane is identified as 3. In the computer tomograph, a calibration phantom 5 comprising inner marking rods and outer point markers 5 is arranged on its bed 6. The infrared cameras 1 detect the spatial position of the calibration phantom 4 via the markers 5, wherein the position of the phantom with respect to the computer tomograph 2 and its image recording plane 3 is also known, since the phantom markings are also visible in the CT cross-sectional images. When the position of the computer tomograph is then detected, also for example via arrangements of markers, the position of the image recording plane 3 in the navigation system can be respectively determined with the aid of the cameras 1, once such a calibration has been performed. This means that it is known at any time during the CT recordings where the cross-sectional image which has just been produced lies, and the advantages already described above can thus be utilised, i.e. the patient can be correctly positioned without a large volume with a lot of patient markings having to be detected in the data set.

The positioning of the patient is correspondingly shown in FIG. 5. By means of the navigation system, which is represented here by the infrared cameras 1, the patient 9 is positioned correctly, together with the bed 11, on the latter. The patients markings having the reference numeral 7 are used here, which are positionally detected by the infrared cameras 1. The position of the treatment target point 10 with respect to the markings 7 is known, and this lies in the recording range of the imaging system, said range having the reference numeral 8. Then, for example either during or directly before recording the first patient data set, the position of the patient can be detected by a computer tomograph by locating the markings 7 outside the recording range of the imaging device. The patient is then positioned such that the recording range 8 enters the image detection range of the computer tomograph, and because of the calibration as described above, the markings 7 do not necessarily also have to be in the image detection range or recording range for exact positioning, and the position of the respective cross-sectional images can nonetheless be exactly determined. Because the distance between the markings can be substantially larger than would be possible if these markings were within the recording range, highly exact positioning is possible.

What is claimed is:

1. A method for producing or updating an inversely planned radiotherapy plan for fractionated radiation exposure of a patient, wherein an up-to-date radiotherapy plan is calculated using volume-dose histograms, the up-to-date radiotherapy plan being at least partly calculated on the basis of an already existing, approved, older plan for the same patient, the patient being subjected to an imaging method before each radiotherapy session over a duration of the fractionated radiation exposure, and wherein the calculation of the up-to-date radiotherapy plan is carried out using new image data created thereby, and wherein, for transferring a radiotherapy plan onto a more recent planning data set, the position and form of a target volume and the organs to be protected are fully or partly fused automatically into the new plan from the old plan.

2. A method as set forth in claim 1, wherein the fusion involves a graphic elastic morphing method of the information to be fused.

3. A method for producing a session treatment plan for fractionated radiation exposure of a patient following production of an inversely planned radiotherapy treatment plan based on dosage distributions for a target volume and organ that have been previously approved by a physician or physicist, comprising the steps of:

(a) using a more current image data set of a target volume of a patient and an organ of the patient to be protected to update the positions of the target volume and organ in a previously acquired image data set to obtain an updated image data set;

(b) using the previously approved dosage distributions to define constraints for volume-dosage histograms to be used to calculate a new session treatment plan for fractionated radiation exposure of the patient; and (c) calculating the new session treatment plan using the constraints and the updated image data set; and wherein the position and form of the target volume and organ are fully or partly adopted automatically into the updated image data set; wherein the adopted information is transferred by means of a three-dimensional fusion of the contours, drawn in by hand, onto layers or voxels of the updated image data set; and wherein the fusion is effected by a graphic elastic morphing method.

4. A method for producing a session treatment plan for fractionated radiation exposure of a patient following production of an inversely planned radiotherapy treatment plan based on dosage distributions for a target volume and organ that have been previously approved by a physician or physicist, comprising the steps of:

(a) using a more current image data set of a target volume of a patient and an organ of the patient to be protected to update the positions of the target volume and organ in a previously acquired image data set to obtain an updated image data set;

(b) using the previously approved dosage distributions to define constraints for volume-dosage histograms to be used to calculate a new session treatment plan for fractionated radiation exposure of the patient; and (c) calculating the new session treatment plan using the constraints and the updated image data set: and wherein automatic fusion is used to update the positions of the target volume and organ in the previously acquired image data set to obtain an updated image data set.

5. A method as set forth in claim 4, comprising the step of (d) comparing the new session treatment plan with the previously approved treatment plan obtained using the previously approved dosage distributions to determine if the deviations fall within specified tolerance range.

6. A method as set forth in claim 5, comprising the step of (e) carrying out the new session treatment plan if the deviations fall within the pre-defined tolerance range without re-evaluation and approval of the new session treatment plan by a physician or physicist.

7. A method as set forth in claim 6, wherein steps (a) through (e) are repeated during multiple fractionated radiotherapy treatment sessions.

8. A method as set forth in claim 6, wherein the patient is subjected to an imaging method before each fractionated radiotherapy treatment session to obtain a current image data set for each respective session.

9. A method as set forth in claim 6, wherein the new session treatment plan is automatically qualified as an approved plan if the deviations fall within the pre-defined tolerance range.

10. A method as set forth in claim 9, wherein steps (a) through (e) are repeated during multiple fractionated radiotherapy treatment sessions.

11. A method as set forth in claim 4, comprising the step of acquiring the current image data set of the target volume and the organ by subjecting the patient to an imaging method.

12. A method as set forth in claim 11, wherein the position of the patient relative to the imaging device is detected by the use of locating markers outside the region of the patient being imaged by the imaging device.

13. A method as set forth in claim 12, wherein the system for locating the markers is calibrated relative to the imaging device, such that the position of the markers can be determined relative to a data set recorded by the imaging device.

14. A method as set forth in claim 4, wherein the imaging method is a CT or MR image recording method.

15. A method as set forth in claim 4, wherein the position and form of the target volume and organ are fully or partly adopted automatically into the updated image data set.

16. A method as set forth in claim 15, wherein the adopted information is transferred by means of a three-dimensional fusion of the contours, drawn in by hand, onto layers or voxels of the updated image data set.

* * * * *